US009703325B2

(12) United States Patent
Pope et al.

(10) Patent No.: US 9,703,325 B2
(45) Date of Patent: Jul. 11, 2017

(54) COVERGLASS FRACTURE DETECTION

(71) Applicant: Apple Inc., Cupertino, CA (US)

(72) Inventors: Benjamin J. Pope, Sunnyvale, CA (US); Miguel C. Christophy, San Francisco, CA (US)

(73) Assignee: APPLE INC., Cupertino, CA (US)

( * ) Notice: Subject to any disclaimer, the term of this patent is extended or adjusted under 35 U.S.C. 154(b) by 26 days.

(21) Appl. No.: 14/825,160

(22) Filed: Aug. 12, 2015

(65) Prior Publication Data
US 2017/0045915 A1    Feb. 16, 2017

(51) Int. Cl.
*G06F 3/041* (2006.01)
*G06F 1/16* (2006.01)
*G01N 29/04* (2006.01)
*G01N 21/41* (2006.01)
*G01N 21/958* (2006.01)

(52) U.S. Cl.
CPC .......... *G06F 1/1656* (2013.01); *G01N 21/41* (2013.01); *G01N 21/958* (2013.01); *G01N 29/04* (2013.01); *G06F 1/1637* (2013.01); *G06F 3/0416* (2013.01); *G01N 2201/062* (2013.01); *G01N 2291/0232* (2013.01); *G01N 2291/0289* (2013.01)

(58) Field of Classification Search
None
See application file for complete search history.

(56) References Cited

U.S. PATENT DOCUMENTS

| 3,557,950 | A | | 1/1971 | Powers | |
|---|---|---|---|---|---|
| 3,713,127 | A | * | 1/1973 | Keledy | G01N 29/14 340/540 |
| 4,112,420 | A | * | 9/1978 | Mifune | G08B 13/1609 340/550 |
| 5,767,454 | A | * | 6/1998 | Goodwin, III | G01G 23/00 177/45 |
| 6,111,638 | A | | 8/2000 | Chou | |
| 6,286,361 | B1 | * | 9/2001 | Jones | F01D 5/18 73/24.05 |
| 8,873,028 | B2 | | 10/2014 | Sheldon et al. | |
| 9,038,469 | B2 | * | 5/2015 | Sohn | G01N 29/043 73/598 |

(Continued)

FOREIGN PATENT DOCUMENTS

CN   103942777   7/2014

*Primary Examiner* — Fekadeselassie Girma
(74) *Attorney, Agent, or Firm* — Brownstein Hyatt Farber Schreck, LLP

(57) ABSTRACT

This application relates to methods and apparatus for detecting and characterizing the formation of cracks in a display cover. Various types of sensors can be used to accomplish the described embodiments. For example, a touch sensor can be utilized for detection and characterization purposes. Alternatively, a crack detection specific sensor or sensors can be added to a device. In some embodiments, when formation of a crack is detected, a device having a sensor that detects a crack can adjust its behavior depending upon how the crack is characterized. For example, the device can be configured to notify a user of the device of any or all systems of the device that will be affected by the detected crack. In some embodiments, crack characterization data can be sent to a device manufacturer to improve subsequent device models.

19 Claims, 8 Drawing Sheets

(56) References Cited

U.S. PATENT DOCUMENTS

| | | | |
|---|---|---|---|
| 2002/0101173 A1* | 8/2002 | Tsai | G09G 3/298 315/169.3 |
| 2007/0048084 A1* | 3/2007 | Jung | G09F 9/30 404/9 |
| 2009/0237374 A1* | 9/2009 | Li | G06F 3/0414 345/174 |
| 2009/0309616 A1* | 12/2009 | Klinghult | G06F 3/044 324/686 |
| 2010/0225497 A1* | 9/2010 | Marincak | G01N 27/24 340/657 |
| 2010/0327441 A1* | 12/2010 | Suehiro | H01L 23/49816 257/738 |
| 2011/0117955 A1* | 5/2011 | Lee | H04M 1/72569 455/550.1 |
| 2012/0109560 A1* | 5/2012 | Huang | G01M 5/0091 702/75 |
| 2013/0082970 A1* | 4/2013 | Frey | G06F 3/0414 345/173 |
| 2013/0127606 A1* | 5/2013 | Chang | G09G 3/006 340/384.7 |
| 2013/0144797 A1* | 6/2013 | Bowles | G06Q 30/0278 705/306 |
| 2013/0154842 A1* | 6/2013 | Chishima | G06F 3/0416 340/665 |
| 2014/0102201 A1* | 4/2014 | Brignac | G01N 29/041 73/592 |
| 2015/0146069 A1* | 5/2015 | Yamazaki | H04N 5/23293 348/333.01 |
| 2015/0200351 A1* | 7/2015 | Zawada | H01L 41/183 252/62.9 PZ |
| 2015/0255740 A1* | 9/2015 | Nakada | H01L 51/0097 257/40 |
| 2016/0004344 A1* | 1/2016 | Lee | G06F 3/044 345/174 |
| 2016/0200086 A1* | 7/2016 | Dolezal | B32B 7/02 428/203 |
| 2016/0267826 A1* | 9/2016 | Seo | G09G 3/006 |
| 2016/0293884 A1* | 10/2016 | Zhang | H05B 33/0896 |

* cited by examiner

A-A

COVERGLASS FRACTURE DETECTION

FIELD

The described embodiments relate generally to methods for detecting damage to a portable electronic device. More particularly, the present embodiments include methods and apparatus for detecting the creation of cracks in a display cover of the portable electronic device and for modifying behavior of the portable electronic device in response to the detection.

BACKGROUND

Portable electronic devices are generally built to withstand any number of stresses and strains caused by daily use. Due to the portable nature of these devices, the portable electronic devices are likely to be subjected to drops and impacts of varying severities. While various ways of reinforcing and strengthening these devices to account for these types of events have been developed, certain portions of the devices can still remain quite susceptible to breakage and/or degradation. In particular, the display cover or coverglass portion of a portable electronic device can be an area in which damage is likely when the portable electronic device is dropped or subjected to a high impact force. Forces acting upon the coverglass can cause any number of different types of breaks and/or cracks to occur in the coverglass. Unfortunately, device designers are often unable to get much data about how and in what circumstances a coverglass component is most likely to break. For this reason, the device designers do not always have the data necessary to add features to the device that can help to mitigate coverglass breakage in common fall scenarios.

SUMMARY

This paper describes various embodiments that relate to systems suitable for detecting and characterizing cracks propagating through a display cover of a portable electronic device.

A portable electronic device is disclosed. The portable electronic device includes at least the following: a device housing; a display cover coupled with the device housing; a processor; and a crack detection system disposed within the device housing and electrically coupled with the processor. When the crack detection system detects a crack in the display cover, the processor alters operation of the portable electronic device.

Another portable electronic device is disclosed. The portable electronic device includes at least the following: a housing including a housing component and a display cover; a display assembly disposed beneath the display cover; a crack detection sensor arranged adjacent to the display assembly. The crack detection sensor periodically measures light refracted by the display cover during operation of the portable electronic device.

An electronic device is disclosed. The electronic device includes at least the following: a device housing; a display cover overlaying a display assembly disposed within the device housing; a device orientation system; and a crack detection system. The crack detection system is configured to change from a first state to a second state in response to determination by the device orientation system that an event likely to damage the display cover is imminent or has just occurred.

Other aspects and advantages of the invention will become apparent from the following detailed description taken in conjunction with the accompanying drawings which illustrate, by way of example, the principles of the described embodiments.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1A:
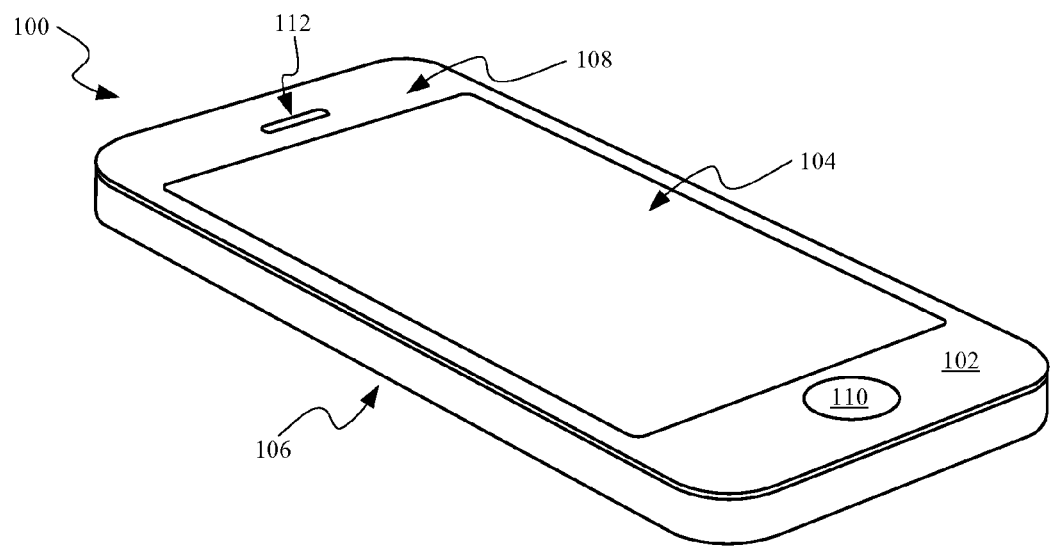
FIG. 1A shows an exemplary device suitable for use with the described embodiments.

Representative applications of methods and apparatus according to the present application are described in this section. These examples are being provided solely to add context and aid in the understanding of the described embodiments. It will thus be apparent to one skilled in the art that the described embodiments may be practiced without some or all of these specific details. In other instances, well known process steps have not been described in detail in order to avoid unnecessarily obscuring the described embodiments. Other applications are possible, such that the following examples should not be taken as limiting.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Portable electronic devices are generally designed to accommodate varying degrees of stress generated by unintentional drops and unintentional impacts. While many systems inside these devices are well protected from an application of moderate force, many devices are most vulnerable to damage resulting from a large impact being applied to a display cover or coverglass. Even though coverglass technology has enjoyed rapid development leading to increasingly durable glass and plastic materials, the coverglass component continues to be one of the most likely components at which a device receives substantial damage when the device is subjected to externally applied forces. Unfortunately, device manufacturers are not always able to determine what event or series of events lead to the formation of a crack or cracks in the coverglass.

One way to help to mitigate problems associated with breakage or damage to the coverglass is to develop a new sensor or adapt an existing sensor for detecting incidents of coverglass breakage. In some embodiments, sensors within the device can be configured to detect any fracture or cracks propagating through the coverglass. Sensors suitable for detection of coverglass breakage can include a touch sensor when the touch sensor is in direct contact with an interior facing surface of the coverglass. Such a configuration can allow for precise determination of a position of any cracks propagating through the coverglass, since any cracks propagating through the coverglass may also separate portions of a sensor grid of the touch sensor. In some embodiments, orientation sensors within the device can be used to generate alerts that direct the device to initiate a scan of the sensors associated with the breakage detection system to determine the following: (1) whether or not there had been a breakage; and (2) how severe any detected fractures had been. For example, when the accelerometer or other spatial/orientation detection sensors detect a deceleration of the device consistent with a fall, those sensors could send a message to the processor. In response to the message, the processor could then initiate a sensor scan for cracks in the display cover. In many embodiments, detection of a crack can be assumed when a significant change in readings from the crack detection system occurs. In some embodiments, data stored within the device can be used to correlate the changes in readings with likely positions of cracks in the display cover.

Once the cracks are detected, any number of actions can be subsequently performed by the device. In some embodiments, a simple message could be sent to a user of the device, informing the user the display glass has been broken. This notification could be very beneficial in cases of a hairline crack where a user might not even realize the presence of a crack. In some embodiments, diagnostic data describing the conditions before and after formation of the crack could be sent to a manufacturer of the device to help optimize future devices so that they are better adapted to resist display cover cracking. In some embodiments, a more detailed message could be sent to a user of the device informing that user of any sensors or systems that would be affected or disabled due to cracking of the display cover. In some embodiments, a user can be asked to confirm a location at which a crack or fracture of the display cover had occurred. Confirmation of the crack could include for example asking the user to confirm a crack location highlighted by a display of the device or asking the user to circle or otherwise indicate a crack location with a touch input.

These and other embodiments are discussed below with reference to FIGS. 1A-6; however, those skilled in the art will readily appreciate that the detailed description given herein with respect to these figures is for explanatory purposes only and should not be construed as limiting.

FIG. 1A shows an exemplary device 100 suitable for use with the described embodiments. As depicted a display cover 102 defines a substantial portion of a top surface of device 100. Display cover 102 can also be referred to as coverglass and can be formed of a durable transparent material along the lines of glass or plastic. Display cover 102 provides a cosmetically and tactilely pleasing surface upon which user inputs can be received. Display cover 102 can overlay display assembly 104, which is contained within and protected by display cover 102 and housing component 106. In some embodiments display assembly 104 can be a touch sensitive display assembly. The touch sensors driving the touch sensitivity can be positioned in many locations. In some embodiments, the touch sensor can be integrated into display assembly 104 and in other embodiments at least a portion of the touch sensor can be applied to an interior facing surface of display cover 102. In some embodiments, masked regions 108 of display cover 102 can be masked by, for example, an amount of ink selectively positioned upon the interior facing surface of display cover 102. The ink can be applied to display cover 102 in a manner so that the only transparent portion of display cover 102 is that portion that overlays an active display portion of display assembly 104. Various colors of ink can be used. Display cover 102 can also define a number of openings. For example, one opening can be configured to allow a user access to button 110. Another opening 112 can be configured to allow audio content generated by a speaker component within housing component 106 to leave device 100 while device 100 is being used as a phone.

Figure 1B:
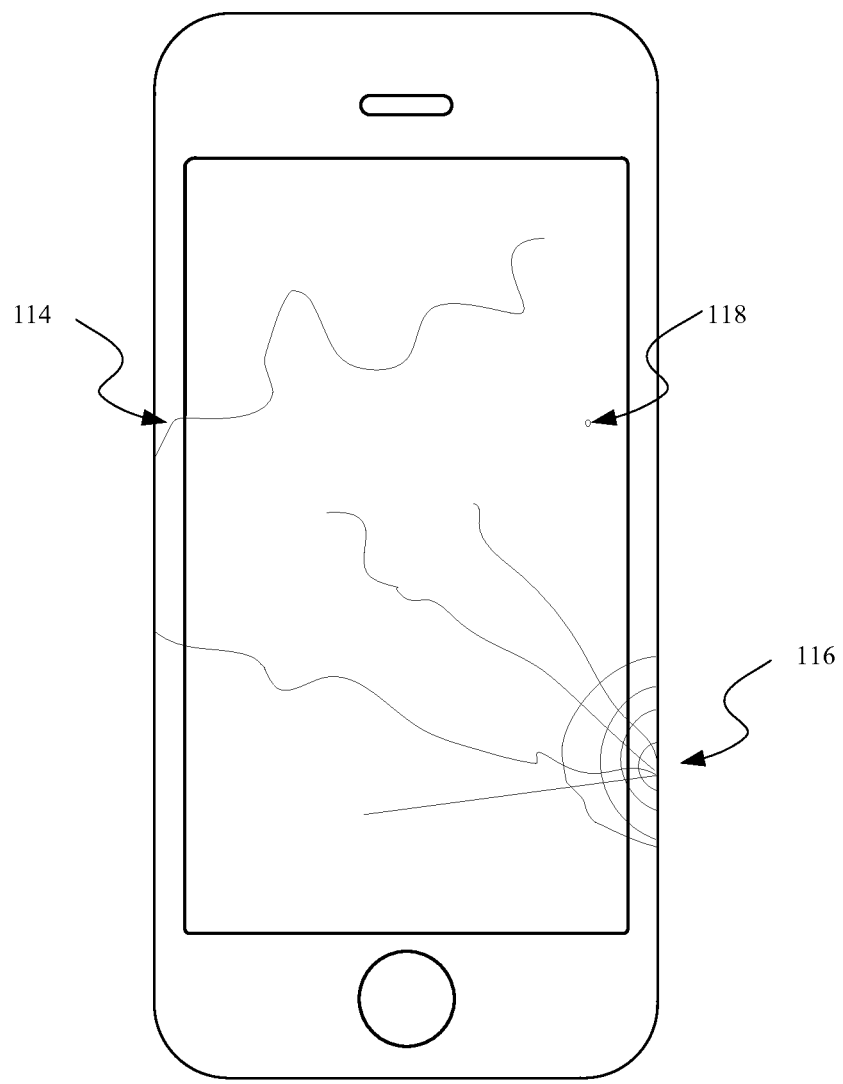
FIG. 1B shows the exemplary device depicted in FIG. 1A after a number of cracks have propagated through a display cover of the exemplary device.

FIG. 1B shows the exemplary device depicted in FIG. 1A after a number of cracks have propagated through display cover 102. The cracks depicted in FIG. 1B show different types and severities of cracking. Hairline crack 114 is a single line crack that can have less impact upon a device than webbed cracking 116. With webbed cracking a lattice of cracks can be formed from a severe enough impact, in some cases causing substantial chips of glass to be released from device 100. In some embodiments, a crack detection system disposed within device 100 can be configured to distinguish between hairline and webbed cracking. In some embodiments the crack detection system can also determine what percentage of display cover 102 is covered in cracks. In still other embodiments, crack detection systems can be configured to detect the presence of chipped area 118 appearing along an exterior surface of display cover 102. The device could be configured to reassure a user when a chipped area of display cover 102 does not extend entirely through display cover 102. In such a case a user can be reassured when no other impacts to functionality of the device result.

Figure 2:
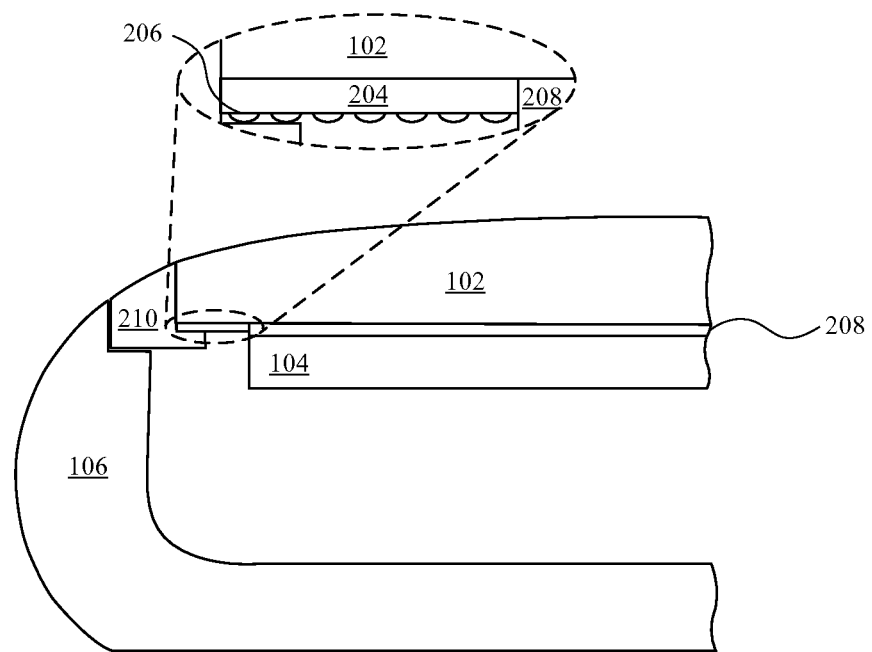
FIG. 2 shows a partial cross-sectional view of the exemplary device.

FIG. 2 shows a partial cross-sectional view of electronic device 100. In some embodiments, display cover 102 can include a number of masked regions 108 as depicted in FIG. 1A. Masked regions 108 can be defined by masking material 204 disposed upon an interior facing surface of display cover 102. Masking material 204 can take many forms including optically opaque paint or ink. In some embodiments, capacitive elements 206 can take the form of indium tin oxide or silver ink/particles. Indium tin oxide has the advantage of being optically transparent and electrically conductive. In some embodiments, a touch sensor array associated with display assembly 104 is used to detect and characterize cracks in display cover 102. This configuration can be used when the touch sensor array is in direct contact with an interior facing surface of display cover 102. When a crack propagates through display cover 102, the cracking can also sever connections in the touch sensor array. These severed connections in the touch sensor array can be monitored to obtain detailed information about propagation of the cracks.

Display assembly 104 can be coupled to display cover 102 by adhesive layer 208. In some embodiments, adhesive layer 208 can be a liquid optically clear adhesive so that transmission of an image produced by display assembly 104 is not obscured. In some embodiments, an interface between display cover 102 and housing component 106 can be formed by environmental seal 210, which can help to prevent the passage of foreign objects or contaminates between display cover 102 and housing component 106. It should be noted that if the touch sensor is limited to an area overlaying display assembly 104, then the use of the touch sensor as the sole means of monitoring cracking of display cover 102 would limit the ability of the devices ability to detect and characterize cracks forming in masked regions 108 of display cover 102. In some embodiments, substantially all of display cover 102 can be monitored for cracks by combining inputs from a touch sensor associated with display assembly 104 and capacitive elements 206 taking the form of beads of silver ink or particles embedded within masked regions 108. In some embodiments, a touch sensor associated with display assembly 104 can expanded out past an active display region of display assembly 104 so that the touch sensor covers both the portion of display cover 102 that overlays an active display region of display assembly 104 and masked regions 108 of display cover 102. In this way, any cracking of any portion of display cover 102 can be monitored. It should be noted that in embodiments, where a touch sensor is integrated with display assembly 104, additional sensors may be needed to monitor portions of display cover 102 overlaying the active display region of display assembly 104. In some embodiments, display cover 102 can include indium tin oxide particles adhered to or embedded within display cover 102 to accomplish the function of monitoring for cracks propagating through display cover 102.

Figure 3A:
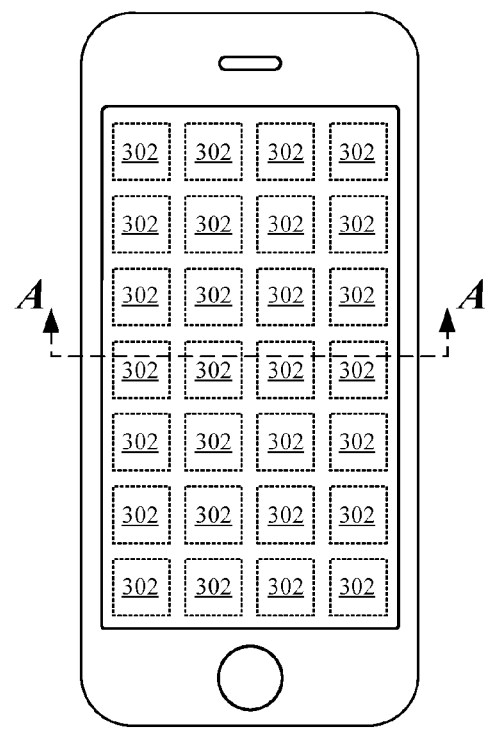
FIG. 3A shows a top view of a coverglass fracture detection system in which an array of piezoelectric actuators are attached to the display assembly.
Figure 3B:
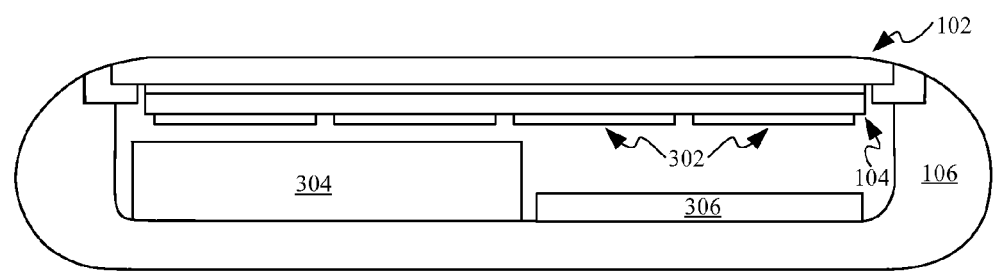
FIG. 3B shows a cross-sectional view of the coverglass fracture detection system of FIG. 3A.

FIGS. 3A-3B show another coverglass fracture detection embodiment in which an array of piezoelectric actuators are positioned below display assembly 104. FIG. 3A shows a top view of electronic device 100 and how piezoelectric actuators 302 can be arranged in a grid pattern within electronic device 100. In this way, piezoelectric actuators 302 can send out vibrations targeted at various portions of display cover 102. While the sensors are only shown below the display portion it should be understood that they could also be arranged beneath masked portions. By using an additional sensor or one integrated within piezoelectric actuator 302 to measure the vibrations returned by the display cover a baseline can be created either upon manufacturing completion or periodically during operation of the device to account for any minor changes due to wear on the device. By periodically monitoring the vibratory response of different portions of display cover 102, substantial differences in the vibratory response can be detected and classified as cracks or potential cracks. Periodic monitoring of the display cover response to the vibrations can even include embodiments in which the vibratory response is measured subsequent to use of one or more piezoelectric actuators for other operational purposes. In some embodiments, other sensors can be combined with this detection method to further refine crack data detected in this way. In some embodiments, these checks can be limited to situations in which a fall or drop event has occurred since vibration of each actuator can affect the user experience and if done at frequent intervals even adversely affect battery life.

FIG. 3B shows a cross-sectional view of device 100 in accordance with section line A-A of FIG. 3A and shows how piezoelectric actuators 302 can be positioned along an interior facing surface of display assembly 104. By packaging piezoelectric actuators 302 in a thin form factor the piezoelectric actuators can have only a minor effect on overall free space available within the device for other components or space for cooling channels. Components disposed within device 100 can include for example, battery 304 and printed circuit board 306. It should be noted that while an array of piezoelectric actuators are depicted that in some embodiments a single vibratory motor could be used and that changes in the vibratory response could be used as a first indication of the presence of a crack in the display cover when the vibratory response of the display cover is substantially different. For example, in some embodiments a unitary vibratory motor can be configured to record a response of the display cover to vibrations generated by the vibratory motor.

Figure 4A:
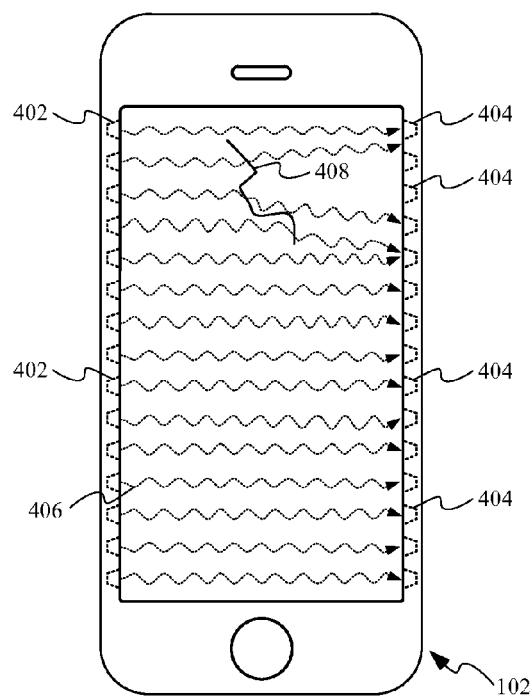
FIG. 4A shows an embodiment in which light is utilized to detect and characterize cracks propagating through the display cover.

FIG. 4A shows an embodiment in which light is utilized to detect and characterize cracks propagating through display cover 102. In FIG. 4A, electronic device 100 is depicted having an array of light emitting devices 402 arranged at one end of display cover 102 that emit light that travels across display cover 102. In some embodiments, light emitting devices 402 take the form of light emitting diodes and can transmit light through display cover 102 without substantially effecting output of display assembly 104 through display cover 102. In configurations where continuous illumination of display cover 102 by light emitting devices 402 does effect the output of display assembly 104, light emitting devices 402 can be configured to emit only short bursts of light 406 unlikely to affect display output. One advantage of periodically pulsing the light is that an amount of energy expended by light emitting devices 402 can be minimized. In some embodiments, as described above light emitting devices 402 may only emit light 406 in response to some other stimulus, such sensor readings showing indications of drop and/or shock events. Light detecting devices 404 can be arranged opposite light emitting devices 402 and can characterize how much and in what direction light emitted from light emitting devices 402 arrives at light detecting devices 404. In some embodiments, light 406 from light emitting devices 402 can be polarized so that any change in orientation of the light waves by cracks and/or imperfections in the glass are further accentuated. In some embodiments, light 406 emitted by the light emitting device 402 can be pulsed in a recognizable pattern so that light from light emitting devices 402 can be differentiated from light entering display cover 102 from another source. For example, circuitry associated with light detecting devices 404 can be arranged to ignore any detected light not pulsed at a predetermined frequency. When the pulse modulation of the light beam is different for each light emitting device 402, the differences in pulse modulation can also be used to determine which light emitting device 402 emitted the detected light to better help characterize defects within display cover 102. In some embodiments, both light emitting devices 402 and light detecting devices 404 can both be configured to both emit and detect light. It should also be noted that while numerous emitters and detectors are depicted, the system can be configured to operate with as few as one emitter and one detector. FIG. 4A also shows how crack 408 diverts some of light 406 as it exits crack 408. The deflection of light 406 from a path it would normally take in the absence of crack 408 can be used to determine at least an approximate location of crack 408.

Figure 4B:
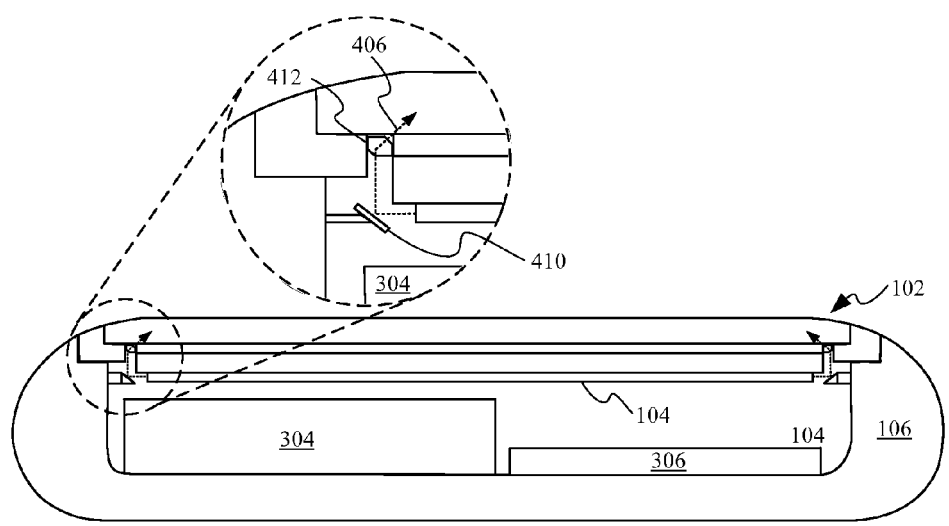
FIG. 4B shows an additional embodiment in which light from within the exemplary device is redirected so that the light refracts through the display cover.

FIG. 4B shows an additional embodiment in which light from within device 100 is redirected so that the light refracts through display cover 102. This variation can be accomplished by distributing prisms and/or mirrors within device 100. In some embodiments, as depicted, light 406 bleeding out of peripheral edges of display assembly 104 can be redirected by mirror 410 and prism 412. In other embodiments, light emitting devices 402 can be embedded farther away from display cover 102 and using mirrors 410 and/or prisms 412 the light from light emitting devices 402 can be redirected to enter at or near one end of display cover 102. The light detection method may have the advantage of being able to detect chips in display cover 102 in addition to hairline fractures and cracks that propagate through an interior surface of display cover 102. It should be noted that in some embodiments, an existing sensor along the lines of an ambient light sensor can be configured to detect changes in reflectance of nearby portions of display cover 102.

Figure 5:
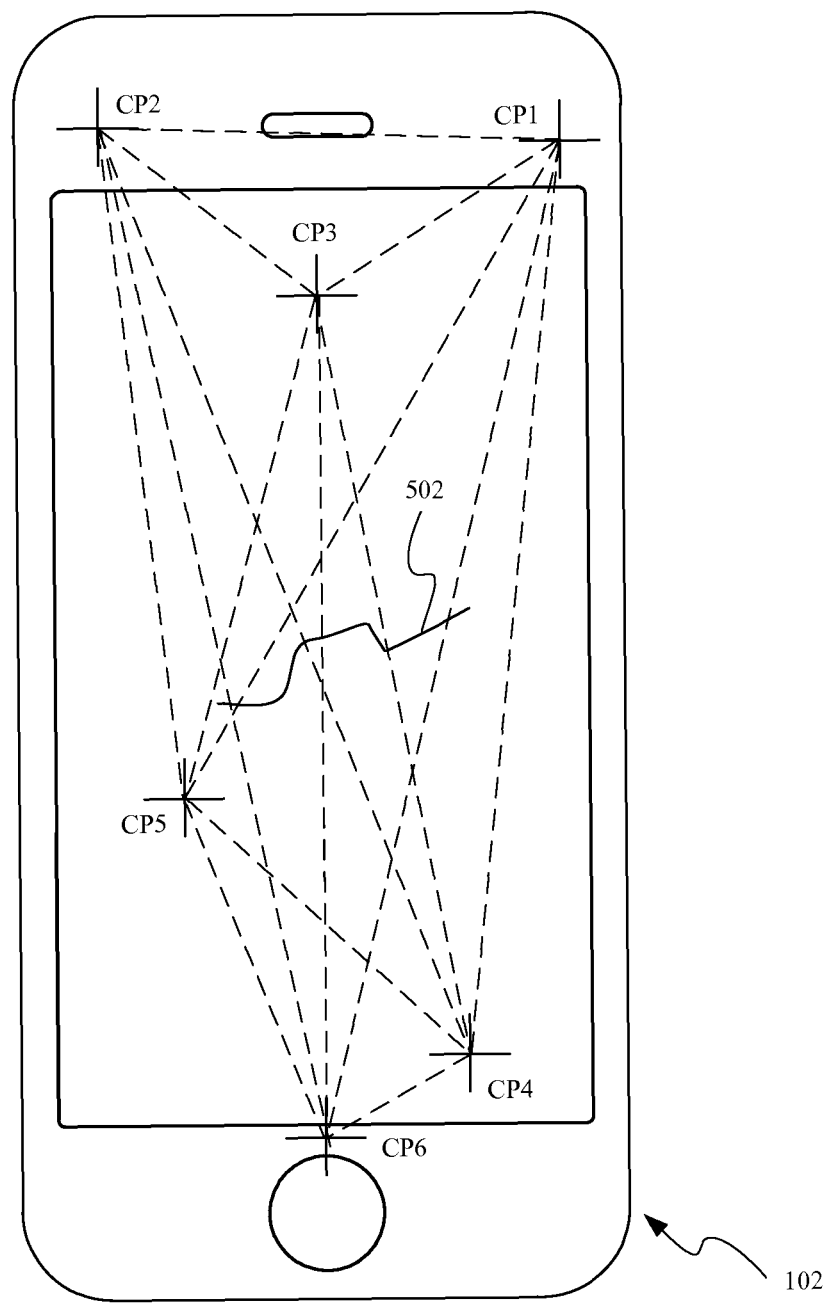
FIG. 5 shows another way in which cracks or fractures forming in the display cover can be characterized.

FIG. 5 shows another way in which cracks or fractures forming in display cover 102 can be characterized. An array of contact points CP1-CP6 can be distributed across display cover 102 as depicted. Each of the contact points can be configured to measure a resistance of display cover 102 between contact points. A change in resistance between the contact points can be indicative of crack formation between the contact points. For example, when a fracture or crack 502 runs through the direct path between each of the contact points, represented by the dotted lines the electrical resistance can change. This change in resistance can be detected and interpreted by a processor as a signal By receiving the various signals and determining which contact points do or do not experience changed resistances a location of the crack can at least be approximated. For example, because resistance between CP1, CP2 and CP3 the crack is not running through an upper portion of display cover 102. By adding a larger numbers of contact points characterization of crack 502 can be accomplished with greater precision. While the contact points are distributed in both active and masked portions of display cover 102 it should be appreciated that the contact points can be arranged entirely within the masked portions or the active portions. It should be understood that feedback from each of the contact points can be communicated to additional circuitry disposed on for example a printed circuit board below display cover 102 by way of a flexible circuit extending from a connector or connection point on display cover 102 and a connector on the printed circuit board.

Figure 6:
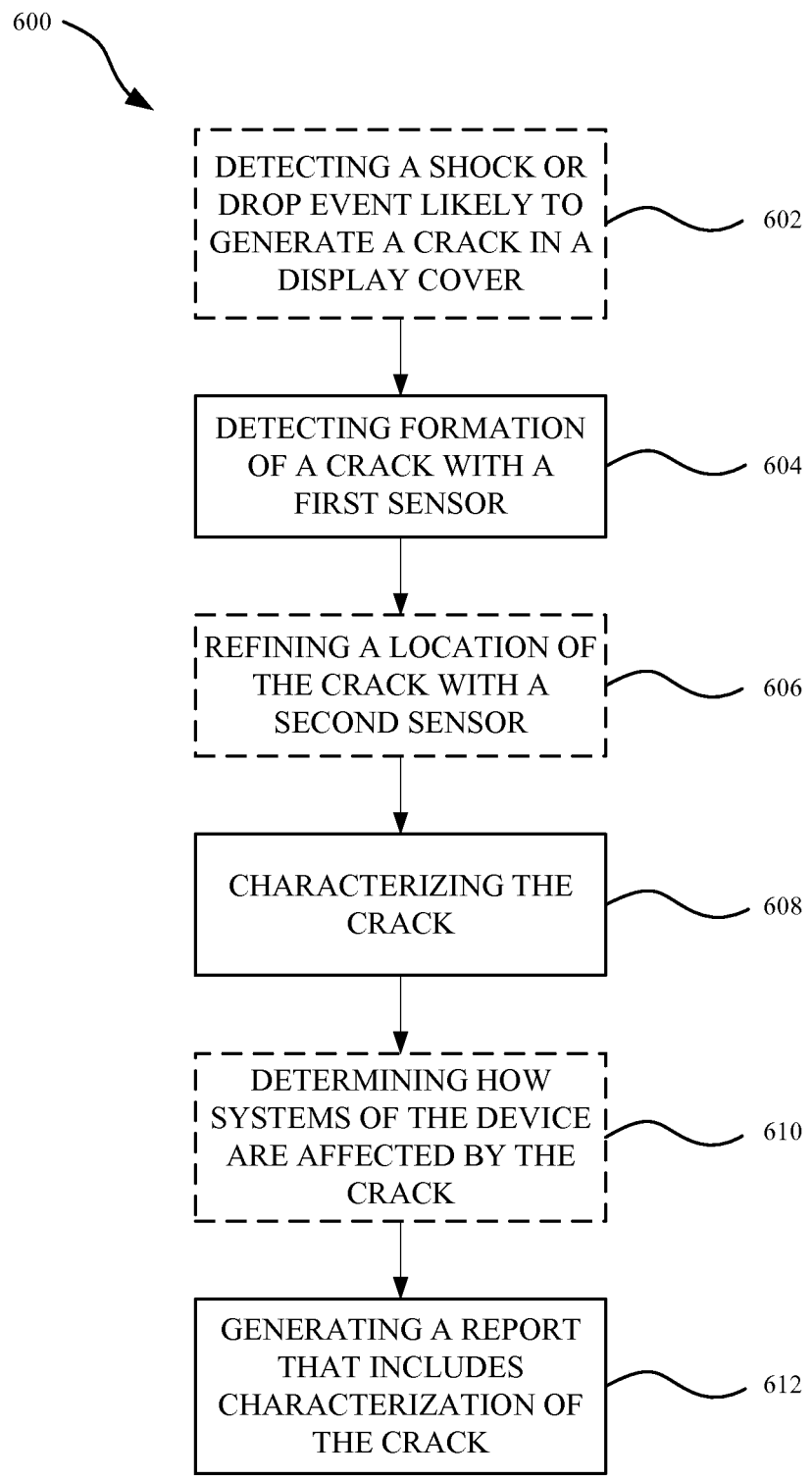
FIG. 6 shows a flowchart depicting a method for detecting the propagation of cracks in a display cover of an electronic device.

FIG. 6 shows a flow chart depicting a method 600 for characterization of a crack in a display cover. In a first optional step 602, motion sensors of an electronic device along the lines of accelerometers, gyroscopes and barometers can all be utilized together or individually to provide real-time feedback regarding physical positioning, orientation and forces acting upon a device. These inputs can be used to identify situations in which a crack is likely to be formed in a display cover. For example, when the accelerometer detects a device is in free fall, sensors can be activated to gather detailed information just prior to and after an impact ending the free-fall event. At step 604, crack detection specific sensors may only be activated or configured to send crack sensing data to a processor when cued by the aforementioned orientation sensors. In other embodiments, the crack detection specific sensors can begin sampling at higher rates when cued by the motion sensors. At optional step 606, an additional sensor or sensors can be activated in response to the first sensor determining the propagation of at least one crack or fracture in the display cover. The additional sensor can be configured to provide additional detail and/or different characteristics regarding the detected crack than the one initially detected by the first sensor. At step 608, the characterization data received by the first and/or second sensors can be transmitted to a processor for analysis. Once the processor analyzes depth, length, width and propagation rate data collected from the sensors, additional actions can be taken. At optional step 610, the crack propagation data can be used to determine whether any systems of the device are affected by formation of the crack. In some embodiments, the certain functionality of the device can be disabled to avoid inaccurate readings or to prevent additional damage to the device. At step 612, the crack creation/propagation data can be associated with any motion data collected and sent out as diagnostic data for collection by device manufacturers, or in some embodiments sent off to warranty entities to assist in making warranty eligibility determinations. In some embodiments, a user can be prompted to confirm locations of cracks identified by the sensor system. In other embodiments, a user could be asked to provide brief survey results regarding in what way the device had incurred its cracks/fractures. In some embodiments, in addition to or in lieu of sending diagnostic data, a message can be sent to a user of the device alerting that user of any problems or reduced functionality being caused by the crack.

Figure 7:
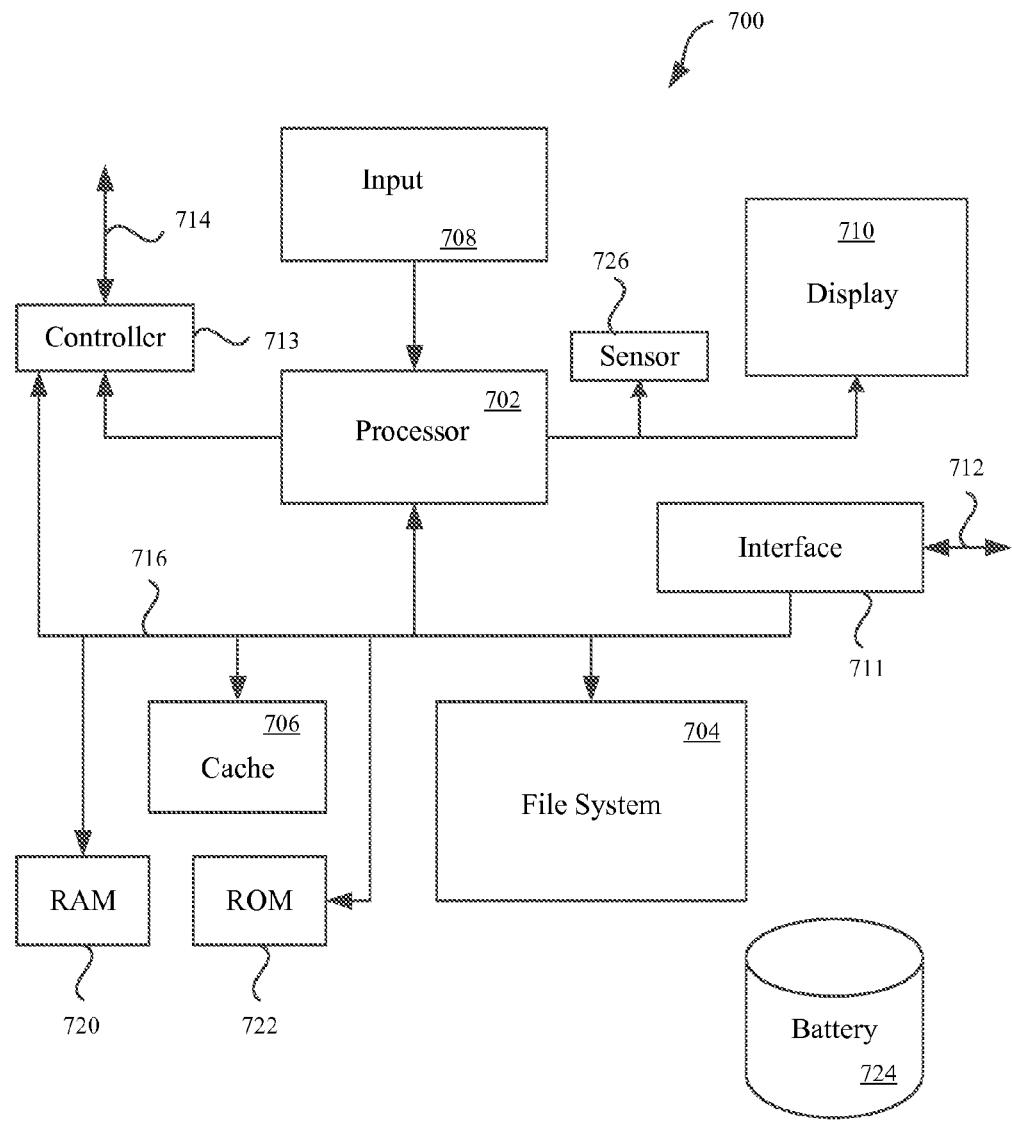
FIG. 7 shows a block diagram of an electronic device suitable for use with the described embodiments.

FIG. 7 is a block diagram of an electronic device suitable for controlling some of the processes in the described embodiment. Electronic device 700 can illustrate circuitry of a representative computing device. Electronic device 700 can include a processor 702 that pertains to a microprocessor or controller for controlling the overall operation of electronic device 700. Electronic device 700 can include instruction data pertaining to operating instructions in a file system 704 and a cache 706. File system 704 can be a storage disk or a plurality of disks. In some embodiments, file system 704 can be flash memory, semiconductor (solid state) memory or the like. The file system 704 can typically provide high capacity storage capability for the electronic device 700. However, since the access time to the file system 704 can be relatively slow, the electronic device 700 can also include cache 706. The cache 706 can include, for example, Random-Access Memory (RAM) provided by semiconductor memory. The relative access time to the cache 706 can substantially shorter than for the file system 704. However, cache 706 may not have the large storage capacity of file system 704. Further, file system 704, when active, can consume more power than cache 706. Power consumption often can be a concern when the electronic device 700 is a portable device that is powered by battery 724. The electronic device 700 can also include a RAM 720 and a Read-Only Memory (ROM) 722. The ROM 722 can store programs, utilities or processes to be executed in a non-volatile manner. The RAM 720 can provide volatile data storage, such as for cache 706.

Electronic device 700 can also include user input device 708 that allows a user of the electronic device 700 to interact with the electronic device 700. For example, user input device 708 can take a variety of forms, such as a button, keypad, dial, touch screen, audio input interface, visual/image capture input interface, input in the form of sensor data, etc. Still further, electronic device 700 can include a display 710 (screen display) that can be controlled by processor 702 to display information to the user. Data bus 716 can facilitate data transfer between at least file system 704, cache 706, processor 702, and controller 713. Controller 713 can be used to interface with and control different sensors and electrical components with equipment control bus 714. For example, control bus 714 can be used to control a display of data on a display in addition to audio and/or video output. For example, processor 702, upon a certain event occurring, can supply instructions to control another component through controller 713 and control bus 714. Such instructions can be stored in file system 704, RAM 720, ROM 722 or cache 706.

Electronic device 700 can also include a network/bus interface 711 that couples to data link 712. Data link 712 can allow electronic device 700 to couple to a host computer or to accessory devices. The data link 712 can be provided over a wired connection or a wireless connection. In the case of a wireless connection, network/bus interface 711 can include a wireless transceiver. Sensor 726 can take the form of circuitry for detecting any number of stimuli. For example, sensor 726 can take the form of the crack detection sensor described herein and can provide periodic reports to processor 702, which can be used to adjust overall performance of device 700 in response to a determination that a display cover of display 710 has cracked or fractured. In some embodiments, processor 702 is configured to instruct sensor 726, which can include a number of different crack detection sensors to provide further characterization of a detected crack by using different sensors to characterize it.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling manufacturing operations or as computer readable code on a computer readable medium for controlling a manufacturing line. The computer readable medium is any data storage device that can store data which can thereafter be read by a computer system. Examples of the computer readable medium include read-only memory, random-access memory, CD-ROMs, HDDs, DVDs, magnetic tape, and optical data storage devices. The computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A portable electronic device, comprising:
   a device housing;
   a display cover coupled with the device housing;
   a processor; and
   a crack detection system disposed within the device housing and electrically coupled with the processor;
   a shock detection system for detecting a shock and passing associated shock information to the processor that uses the associated shock information to identify that the device has sustained a shock likely to crack in the display cover;
   wherein when the crack detection system detects a crack in the display cover, the processor alters operation of the portable electronic device.

2. The portable electronic device as recited in claim 1, wherein altering operation of the portable electronic device comprises providing a notification to a user of the portable electronic device that the crack has been detected.

3. The portable electronic device as recited in claim 1, wherein the crack detection system comprises a touch sensor.

4. The portable electronic device as recited in claim 3, wherein the touch sensor is integrated into an interior facing surface of the display cover.

5. The portable electronic device as recited in claim 1, wherein altering operations of the portable electronic device comprises disabling a sensor of the portable electronic device degraded by the detected crack.

6. The portable electronic device as recited in claim 5, wherein the crack detection system comprises an array of conductive traces disposed beneath a masked portion of the display cover.

7. The portable electronic device as recited in claim 1, wherein the crack detection system comprises an array of piezoelectric actuators disposed beneath a display of the portable electronic device.

8. The portable electronic device as recited in claim 7, wherein the array of piezoelectric actuators detect cracks formed in the display cover by measuring vibrations the piezoelectric actuators pulse through the display cover.

9. The portable electronic device as recited in claim 1, wherein the crack detection system only checks for and characterizes cracks when the shock detection system detects a shock or detects movement of the portable electronic device likely to precede a shock.

10. A portable electronic device, comprising:
    a housing including a housing component and a display cover;
    a display assembly disposed beneath the display cover;
    a crack detection sensor arranged adjacent to the display assembly,
    wherein the crack detection sensor periodically measures light refracted by the display cover during operation of the portable electronic device.

11. The portable electronic device as recited in claim 10, wherein the crack detection sensor is a first crack detection sensor and the portable electronic device further comprises a second crack detection sensor that provides a greater amount of information about a crack propagating through the display cover than the first crack detection sensor.

12. The portable electronic device as recited in claim 11, wherein the second crack detection sensor comprises a grid of conductive ink positioned along an interior facing surface of the display cover.

13. The portable electronic device as recited in claim 10, wherein the crack detection sensor comprises a light source and a light detector, the light source being configured to direct light into the display cover and the light detector being configured to measure the light directed into the display cover by the light source.

14. The portable electronic device as recited in claim 13, wherein the light emitted by the light source is modulated to help distinguish the emitted light from other light sources.

15. The portable electronic device as recited in claim 14, further comprising multiple light sources, at least one of the light sources emitting light modulated in a different pattern than the modulation pattern used by the other light sources.

16. An electronic device, comprising:
    a device housing;
    a display cover overlaying a display assembly disposed within the device housing;

a device orientation system; and a crack detection system, wherein the crack detection system is configured to change from a first state to a second state in response to determination by the device orientation system that an event likely to damage the display cover is imminent or has just occurred.

17. The electronic device as recited in claim 16, wherein when the crack detection system is in the first state, the crack detection system checks for cracks at a first interval substantially longer than a second interval at which the crack detection system checks for cracks in the second state.

18. The electronic device as recited in claim 16, wherein the crack detection system comprises a first sensor and a second sensor.

19. The electronic device as recited in claim 18, wherein the first sensor is a touch sensor in contact with an interior facing surface of the display cover.

\* \* \* \* \*